(12) United States Patent
Sturgis et al.

(10) Patent No.: US 10,016,343 B2
(45) Date of Patent: *Jul. 10, 2018

(54) SOLID STICK ANTIPERSPIRANT COMPOSITIONS

(71) Applicant: The Procter & Gamble Company, Cincinnati, OH (US)

(72) Inventors: David Arthur Sturgis, Cincinnati, OH (US); Eric Shane Henley, West Harrison, IN (US); Randall Dudley Griffith, Laura, OH (US); Phi Van Chu, Cincinnati, OH (US); Steven Michael Wujek, Sr., Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 160 days.

This patent is subject to a terminal disclaimer.

(21) Appl. No.: 14/206,067

(22) Filed: Mar. 12, 2014

(65) Prior Publication Data

US 2014/0271515 A1    Sep. 18, 2014

Related U.S. Application Data

(60) Provisional application No. 61/777,255, filed on Mar. 12, 2013.

(51) Int. Cl.
| | | |
|---|---|---|
| A61K 8/02 | (2006.01) |
| A61K 8/58 | (2006.01) |
| A61Q 15/00 | (2006.01) |
| A61K 8/31 | (2006.01) |
| A61K 8/34 | (2006.01) |
| A61K 8/86 | (2006.01) |
| A61K 8/92 | (2006.01) |

(52) U.S. Cl.
CPC .......... *A61K 8/0229* (2013.01); *A61K 8/0216* (2013.01); *A61K 8/31* (2013.01); *A61K 8/342* (2013.01); *A61K 8/58* (2013.01); *A61K 8/86* (2013.01); *A61K 8/922* (2013.01); *A61Q 15/00* (2013.01)

(58) Field of Classification Search
USPC ...................................................... 424/66, 65
See application file for complete search history.

(56) References Cited

U.S. PATENT DOCUMENTS

| | | |
|---|---|---|
| 5,254,332 A | 10/1993 | Grezcyn et al. |
| 5,302,381 A | 4/1994 | Greczyn et al. |
| 5,324,490 A | 6/1994 | Van Vlahakis et al. |
| 5,354,553 A | 10/1994 | Greczyn et al. |
| 5,376,362 A | 12/1994 | Murphy et al. |
| 5,378,452 A | 1/1995 | Greczyn |
| 5,389,279 A | 2/1995 | Au et al. |
| 5,419,879 A | 5/1995 | Vlahakis et al. |
| 5,443,822 A | 8/1995 | Greczyn et al. |
| 5,487,887 A | 1/1996 | Benfatto |
| 5,501,812 A | 3/1996 | Vermeer et al. |
| 5,534,246 A | 7/1996 | Herb et al. |
| 5,575,990 A | 11/1996 | Benfatto |
| 5,603,925 A | 2/1997 | Ross et al. |
| 5,650,140 A | 7/1997 | Bergmann et al. |
| 5,650,141 A | 7/1997 | Bergmann et al. |
| 5,650,142 A | 7/1997 | Bergmann et al. |
| 5,650,143 A | 7/1997 | Bergmann et al. |
| 5,733,534 A | 5/1998 | Sawin et al. |
| 5,750,096 A | 5/1998 | Guskey |
| 5,840,286 A | 11/1998 | Gardlik et al. |
| 5,840,287 A | 11/1998 | Guskey et al. |
| 5,840,288 A | 11/1998 | Guskey et al. |
| 5,846,520 A | 12/1998 | Guskey et al. |
| 5,849,276 A | 12/1998 | Guskey et al. |
| 5,861,145 A | 1/1999 | Lucas et al. |
| 5,863,524 A | 1/1999 | Mason et al. |
| 5,928,631 A | 7/1999 | Lucas et al. |
| 5,972,319 A | 10/1999 | Linn et al. |
| 5,997,850 A | 12/1999 | Tang et al. |
| 6,071,975 A | 6/2000 | Halloran |
| 6,110,451 A | 8/2000 | Matz et al. |

(Continued)

FOREIGN PATENT DOCUMENTS

| | | |
|---|---|---|
| DE | 19821691 | 11/1999 |
| DE | 19944545 | 3/2001 |
| DE | 10057767 | 5/2002 |
| EP | 965331 | 12/1999 |
| EP | 1158956 | 12/2001 |
| EP | 1183003 | 3/2002 |
| EP | 1195154 | 4/2002 |
| EP | 2314270 | 4/2011 |
| EP | 1776081 B1 | 8/2011 |
| FR | 2926219 | 7/2009 |
| FR | 2954094 | 6/2011 |
| GB | 2299270 A | 10/1996 |
| JP | 05115538 | 5/1993 |

(Continued)

OTHER PUBLICATIONS

Flick, E., Cosmetic Additives, 1991, Noyes Publications, p. 18.*
U.S. Appl. No. 14/205,924, filed Mar. 12, 2014, Sturgis et al.
U.S. Appl. No. 14/205,872, filed Mar. 12, 2014, Sturgis et al.
U.S. Appl. No. 14/206,134, filed Mar. 12, 2014, Sturgis et al.

*Primary Examiner* — Gina C Justice
(74) *Attorney, Agent, or Firm* — Kathleen Y. Carter

(57) ABSTRACT

A method of manufacturing a packaged solid stick antiperspirant composition is provided. The method includes combining an antiperspirant active, one or more structurants and a surfactant to form a mixture, dispensing the mixture from a nozzle to fill a dispensing package, forming a solid stick antiperspirant composition within the dispensing package. The surfactant has a melt temperature that is greater than the crystallization onset temperature of the solid stick antiperspirant composition. The antiperspirant active and the surfactant are in contact for about 5 minutes or less from the moment that the antiperspirant active and the surfactant and the structurant are mixed until the moment that the mixture is dispensed from the nozzle.

15 Claims, 4 Drawing Sheets

(56) References Cited

U.S. PATENT DOCUMENTS

| | | |
|---|---|---|
| 6,171,601 B1 | 1/2001 | Gardlik et al. |
| 6,187,300 B1 | 2/2001 | Motley et al. |
| 6,277,359 B1 | 8/2001 | Raths et al. |
| 6,383,503 B1 | 5/2002 | Blackmann et al. |
| 6,387,357 B1 | 5/2002 | Chopra et al. |
| 6,436,062 B1 | 8/2002 | Iwamoto et al. |
| 6,436,382 B1 | 8/2002 | Chopra et al. |
| 6,464,991 B1 | 10/2002 | Walele et al. |
| 6,485,716 B1 | 11/2002 | Fei et al. |
| 6,500,412 B1 | 12/2002 | Johansson et al. |
| 6,503,491 B2 | 1/2003 | Guenin et al. |
| 6,511,658 B2 | 1/2003 | Mattai et al. |
| 6,534,045 B2 | 3/2003 | Mattai et al. |
| 6,605,288 B1 | 8/2003 | Okawa et al. |
| 6,608,126 B2 | 8/2003 | Ferritto et al. |
| 6,649,577 B1 | 11/2003 | Bleckmann et al. |
| 6,652,842 B2 | 11/2003 | Lucia et al. |
| 6,652,867 B1 * | 11/2003 | Vincent et al. ............... 424/401 |
| 6,653,378 B2 | 11/2003 | Ferritto et al. |
| 6,703,536 B2 | 3/2004 | Roe et al. |
| 6,716,441 B1 | 4/2004 | Osborne et al. |
| 6,774,179 B2 | 8/2004 | Ferritto et al. |
| 6,787,603 B2 | 9/2004 | Johnson et al. |
| 6,790,435 B1 | 9/2004 | Ma et al. |
| 6,793,929 B2 | 9/2004 | Bleckmann et al. |
| 6,803,399 B2 | 10/2004 | Ferritto et al. |
| 6,821,934 B1 | 11/2004 | Bleckmann et al. |
| 6,835,373 B2 | 12/2004 | Kolodzik et al. |
| 6,835,374 B2 | 12/2004 | Parekh et al. |
| 6,916,465 B2 | 7/2005 | Panzer et al. |
| 6,936,242 B2 | 8/2005 | Elliott et al. |
| 6,942,871 B2 | 9/2005 | Bruning et al. |
| 6,998,424 B2 | 2/2006 | Feng et al. |
| 7,204,976 B2 | 4/2007 | Popoff et al. |
| 7,235,251 B2 | 6/2007 | Hamer et al. |
| 7,452,526 B2 | 11/2008 | Walling et al. |
| 7,799,332 B2 | 9/2010 | Moghe et al. |
| 7,867,506 B2 | 1/2011 | Moghe et al. |
| 8,187,578 B2 | 5/2012 | Walling et al. |
| 8,343,467 B2 | 1/2013 | Woehrmann et al. |
| 8,435,955 B2 | 5/2013 | Masui et al. |
| 8,461,258 B2 | 6/2013 | Iimura et al. |
| 8,546,483 B2 | 10/2013 | Tanaka et al. |
| 2001/0012860 A1 | 8/2001 | Bleckmann et al. |
| 2002/0122781 A1 | 9/2002 | Pinzon et al. |
| 2003/0040571 A1 | 2/2003 | Feng et al. |
| 2003/0082126 A9 | 5/2003 | Pinzon et al. |
| 2003/0103921 A1 | 6/2003 | Brucks et al. |
| 2003/0198653 A1 | 10/2003 | Walele et al. |
| 2004/0166083 A1 | 8/2004 | Abrutyn |
| 2004/0176464 A1 | 9/2004 | Kanatani et al. |
| 2005/0095210 A1 | 5/2005 | Mattai et al. |
| 2005/0118125 A1 | 6/2005 | Mattai et al. |
| 2005/0191257 A1 | 9/2005 | Brahms et al. |
| 2005/0227906 A1 | 10/2005 | Schudel et al. |
| 2005/0288205 A1 | 12/2005 | Walele et al. |
| 2006/0013792 A1 | 1/2006 | Fontaine et al. |
| 2006/0073110 A1 | 4/2006 | Modi |
| 2006/0210502 A1 | 9/2006 | Galante et al. |
| 2006/0280716 A1 | 12/2006 | Czech et al. |
| 2007/0003499 A1 * | 1/2007 | Shen et al. ............... 424/66 |
| 2007/0009472 A1 | 1/2007 | Niebauer et al. |
| 2007/0092541 A1 | 4/2007 | Walling et al. |
| 2007/0166254 A1 | 7/2007 | Bianchi |
| 2009/0016977 A1 | 1/2009 | Modafari et al. |
| 2009/0087396 A1 | 4/2009 | Hwang et al. |
| 2009/0123392 A1 | 5/2009 | Braun et al. |
| 2009/0253612 A1 | 10/2009 | Mushock et al. |
| 2009/0298936 A1 | 12/2009 | Clothier, Jr. et al. |
| 2010/0112017 A1 | 5/2010 | Mizutani et al. |
| 2010/0196515 A1 | 8/2010 | Kamiya et al. |
| 2012/0045493 A1 * | 2/2012 | Popoff et al. ............... 424/401 |
| 2012/0135056 A1 | 5/2012 | Yarlagadda et al. |
| 2012/0205002 A1 | 8/2012 | Walling et al. |
| 2012/0321578 A1 | 12/2012 | Leuridan et al. |
| 2013/0052144 A1 | 2/2013 | Claas et al. |
| 2013/0189204 A1 | 7/2013 | Duggal et al. |
| 2013/0280409 A1 | 10/2013 | Mushock et al. |

FOREIGN PATENT DOCUMENTS

| | | |
|---|---|---|
| JP | 06007415 | 1/1994 |
| JP | 0662060 | 9/1994 |
| JP | 08010314 | 1/1996 |
| JP | 09157147 | 6/1997 |
| JP | 10094591 | 4/1998 |
| JP | 10147793 | 6/1998 |
| JP | 10183172 | 7/1998 |
| JP | 11106315 | 4/1999 |
| JP | 11106330 | 4/1999 |
| JP | 11106781 | 4/1999 |
| JP | 2000186025 | 7/2000 |
| JP | 2000186026 | 7/2000 |
| JP | 2000229826 | 8/2000 |
| JP | 2000300652 | 10/2000 |
| JP | 2003335629 | 11/2000 |
| JP | 2001333968 | 12/2001 |
| JP | 2003081763 | 3/2003 |
| JP | 2003300813 | 10/2003 |
| JP | 2004049889 | 2/2004 |
| JP | 2004137227 | 5/2004 |
| JP | 2004337367 | 12/2004 |
| JP | 2005082484 | 3/2005 |
| JP | 2005145877 | 6/2005 |
| JP | 2006036981 | 2/2006 |
| JP | 2006087903 | 4/2006 |
| JP | 2006298880 | 11/2006 |
| JP | 2007044422 | 2/2007 |
| JP | 2008093207 | 4/2008 |
| JP | 200889783 | 12/2008 |
| JP | 2009001508 | 1/2009 |
| JP | 2009120525 | 6/2009 |
| JP | 2009161474 | 7/2009 |
| JP | 2010141880 | 6/2010 |
| JP | 2011148785 | 8/2011 |
| KR | 20090107340 | 10/2009 |
| KR | 20090129849 | 12/2009 |
| WO | 94/09754 A1 | 5/1994 |
| WO | 96/24326 A1 | 8/1996 |
| WO | 96/37184 A1 | 11/1996 |
| WO | 98/55088 A1 | 12/1998 |
| WO | 00/67713 A1 | 11/2000 |
| WO | 01/13871 A1 | 3/2001 |
| WO | 01/15659 A2 | 3/2001 |
| WO | 2003/53388 | 7/2003 |
| WO | 2003/72610 | 9/2003 |
| WO | 2004/050045 A1 | 6/2004 |
| WO | 2005/099661 A1 | 10/2005 |
| WO | 2007/99738 | 9/2007 |
| WO | 2007/114329 | 10/2007 |
| WO | 2009/138150 | 11/2009 |

* cited by examiner

SOLID STICK ANTIPERSPIRANT COMPOSITIONS

FIELD OF THE INVENTION

The present disclosure generally relates to methods of making solid stick antiperspirant compositions comprising a surfactant.

BACKGROUND OF THE INVENTION

Antiperspirant compositions have become a staple in the personal hygiene routine for many people. These compositions, unlike deodorants, have the added benefit of helping to combat wetness. While wetness is generally harmless, there are social stigmas associated with underarm sweat and feelings of uncleanliness. Various antiperspirant compositions and methods of making are known in the art. Some examples are described in U.S. Pat. Nos. 5,417,964; 5,490,979; 5,603,925; 5,733,534; 5,833,964; 5,972,319; 6,338,840; 6,682,749; 6,752,982; 7,452,526; 8,187,578; 2007/0092541; 2009/0269292; and WO 02/053109. Recently, antiperspirant compositions labeled as clinical strength have become very popular. Providing solid stick antiperspirant compositions having increased wetness protection, which may be desirable for marketing under a clinical strength label, is therefore desirable. Solid stick antiperspirant compositions can be particularly challenging to improve, as many stick type antiperspirant composition contain wax concentrations greater than 10% w/w. As wax concentration increases, wetness protection may decrease as waxes tend to impede water flow into the antiperspirant composition during a sweat event. The use of polar waxes (e.g., stearyl alcohol) may further compound this problem as polar waxes may bind to the antiperspirant active. Soft solid antiperspirant compositions, which typically have lower wax concentrations than solid stick antiperspirant compositions, tend to be better in this regard due to the lower wax concentrations.

There is then room for improvement with respect to the effectiveness of solid stick antiperspirant compositions. Further, there is room for improvement to methods of making solid stick antiperspirant compositions. Still further, there is room to improve the wetness protection of solid stick antiperspirant compositions to more closely approach that of soft solid antiperspirant compositions.

SUMMARY OF THE INVENTION

In accordance with one aspect, a method of manufacturing a packaged solid stick antiperspirant composition is provided. The method includes combining an antiperspirant active, one or more structurants and a surfactant to form a mixture, dispensing the mixture from a nozzle to fill a dispensing package, forming a solid stick antiperspirant composition within the dispensing package. The surfactant has a melt temperature that is greater than the crystallization onset temperature of the solid stick antiperspirant composition. The antiperspirant active and the surfactant are in contact for about 5 minutes or less from the moment that the antiperspirant active and the surfactant and the structurant are mixed until the moment that the mixture is dispensed from the nozzle.

DETAILED DESCRIPTION

I. Definitions

Figure 1:
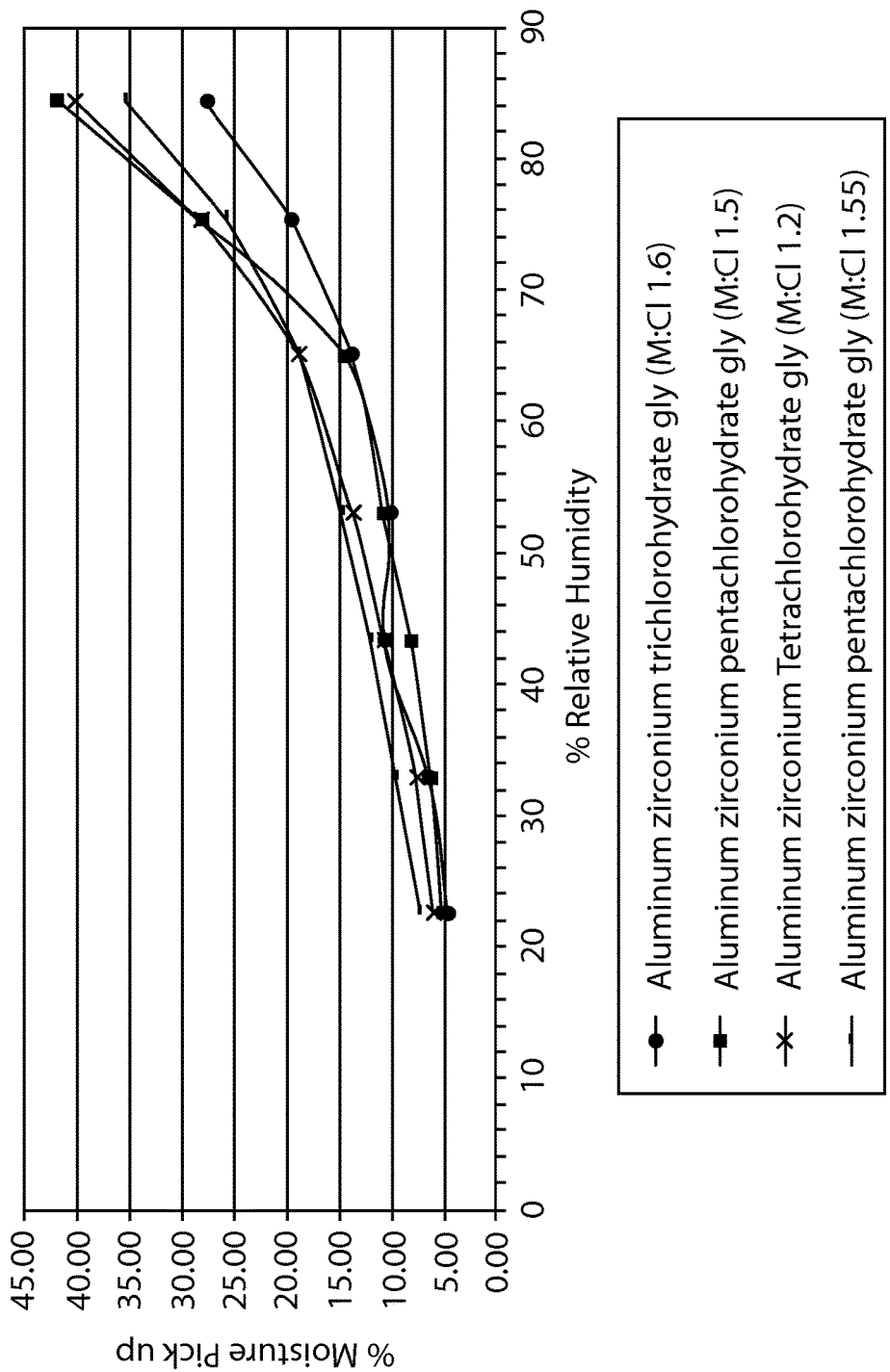
FIG. 1 is graph of hygroscopicity to percentage of relative humidity, wherein four antiperspirant actives having different metal to chloride ratios (M:Cl) are graphed.

Reference within the specification to "embodiment(s)" or the like means that a particular material, feature, structure and/or characteristic described in connection with the embodiment is included in at least one embodiment, optionally a number of embodiments, but it does not mean that all embodiments incorporate the material, feature, structure, and/or characteristic described. Furthermore, materials, features, structures and/or characteristics may be combined in any suitable manner across different embodiments, and materials, features, structures and/or characteristics may be omitted or substituted from what is described. Thus, embodiments and aspects described herein may comprise or be combinable with elements or components of other embodiments and/or aspects despite not being expressly exemplified in combination, unless otherwise stated or an incompatibility is stated.

In all embodiments, all percentages are by weight of the antiperspirant composition (or formulation), unless specifically stated otherwise. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at approximately 25° C. and at ambient conditions, where "ambient conditions" means conditions under about 1 atmosphere of pressure and at about 50% relative humidity. The term "room temperature" refers to 25° C. The term "molecular weight" or "M.Wt." as used herein refers to the number average molecular weight unless otherwise stated.

"Ambient" refers to surrounding conditions at about one atmosphere of pressure, 50% relative humidity and about 25° C.

"Anhydrous" refers to compositions and/or components which are substantially free of added or free water.

"Onset of crystallization" means the temperature at which a material crystallizes from a liquid solution. All melt points and the onset of crystallization referenced herein, unless otherwise specified, are measured by the well known technique of Differential Scanning calorimetry (DSC). For evaluation a Perkin-Elmer 7 Series Thermal Analysis System Model DSC7 is used, manufactured by Perkin-Elmer, Norwalk, Conn.

"Substantially free of" refers to about 2% or less, about 1% or less, or about 0.1% or less of a stated ingredient. "Free of" refers to no detectable amount of the stated ingredient or thing.

"Volatile" means a material that has a boiling point less than 250° C. at standard atmospheric pressure. "Non-volatile" means a material that has a boiling point greater than 250 C at standard atmospheric pressure.

"Wax" refers to materials of any molecular weight that are a solid at room temperature, melt at a temperature between about 40° C. and 130° C. and return to a solid at room temperature.

II. Efficacy Enhancement

Solid sticks and soft solids are two of the more popular forms of antiperspirants compositions. Structurants, like waxes, are used in both of these forms to help give them their structure and stability. The downside to the use of these types of structurants is that they have a tendency to interfere with the release of the antiperspirant active from the composition and thus may negatively impact the efficacy of the composition. This issue is compounded in the solid stick form which may have 3-4 times more structurant than soft solid antiperspirant compositions. Solid sticks typically may have 10% to 25% of structurants whereas soft solids often comprise 3% to 10% of structurants, depending on the method of manufacture.

While reductions in structurant concentration could be used to help increase antiperspirant efficacy, this comes with its own challenges. Reducing the structurant concentration, for example, may negatively impact the stability of the final antiperspirant composition resulting in, for example, syneresis during shipping and or impact its rheology, thereby resulting in possible overdosing of the composition. As such, it is believed to be more desirable to find something that could be added to these types of compositions that would enhance water transport through the composition film after application without negatively impacting stability of the composition. Since soft solid compositions are generally more efficacious due to the much lower amount of structurant, a currently marketed soft solid antiperspirant composition was utilized as a benchmark for comparing the improvement in efficacy of a solid stick antiperspirant composition.

The initial work focused on the addition of surfactants to solid stick compositions to try to improve water transport into and out of the antiperspirant composition during a sweat event. However, this first attempt was unsuccessful. As can be seen in Table 1 below, when a currently marketed solid stick composition (Currently Marketed Solid Stick Composition) was tested against a solid stick composition which included a surfactant (Comparative Solid Stick Composition), the Comparative Solid Stick Composition performed a little worse than the Currently Marketed Solid Stick Composition in the amount of sweat measured versus the benchmark (a current market soft solid composition) in a typical hot room clinical type test. When looking at the results, the less sweat the more efficacious the composition.

TABLE 1

| PRODUCT | SURFAC-TANT | Active/Metal-Chloride Ratio | RESULT |
|---|---|---|---|
| Comparative Solid Stick Composition | Yes | Aluminum zirconium trichlorohydrex about 1.55 | 36 mg more sweat than Current Market Soft Solid |
| Currently Marketed Solid Stick Composition | No | Aluminum zirconium tetrachlorohydrex about 1.2 | 33.5 mg more sweat than Current Market Soft Solid |

The ingredients for the Currently Marketed Solid Stick Composition and the Comparative Solid Stick Composition are set forth below in Table 2.

TABLE 2

| Ingredients | Comparative Solid Stick Composition | Currently Marketed Solid Stick Composition |
|---|---|---|
| SF1202 Silicone Fluid | 26.47 | 29.8 |
| Aluminum Zirconium Trichlorohydrex Gly | 25.48 | |
| Aluminum Zirconium Tetrachlorohydrex Gly | | 25.6 |
| PPG-14 Butyl ether | 6.5 | 6.5 |
| C12-15 Alkyl Benzoate | 9.5 | 8.5 |
| 556 Cosmetic Fluid | 3 | 3 |
| Ozokerite | | 1 |
| Mineral Oil | 1 | |
| Petrolatum | 3 | 3 |
| Stearyl Alcohol | 14 | 13 |
| Castor Wax MP-80 | 3.85 | 2.9 |
| Behenyl Alcohol | 0.2 | 0.2 |
| C20-40 Pareth 10 ethoxylate | 2 | |
| Talc | 3 | 2.5 |
| Cyclodextrin | 2 | 4 |
| | 100 | 100 |

While the initial try was a failure, it wasn't a total surprise as surfactants are sometimes used in these types of solid stick antiperspirants in similar levels as wash off aids without an increase in efficacy.

The impact of the manufacturing process on efficacy and the use of a surfactant was investigated next. Often, solid stick antiperspirant compositions are made in a single batch process. This process may involve adding all of the raw materials (except active and perfume) to a mix tank, heating it to a temperature to melt the structurants and other higher melt point ingredients, and holding it at that temperature until the appropriate ingredients are melted. This heating step can involve temperatures of, for example, 80° C. or more, and it can take from 45 minutes to an hour for the ingredients to melt. At this point, the batch is cooled to 70-75° C. and the active and perfume are added to the tank. The composition is usually mixed here for at least 15 minutes before it is eventually cooled to 50-55° C. and poured into canisters.

There are, however, some commercial solid stick antiperspirant compositions which are made using another method. In this method, there is generally a hot process stream and a cold process stream. The hot process stream generally involves mixing a solvent and structurant in a batch tank which is heated to a first temperature sufficient to melt the waxes. The cold process stream generally involves mixing a solvent, an antiperspirant active, and any heat sensitive ingredients in batch tank at a lower temperature. The two streams, from each batch tank, are then combined in such a way as to cause substantially complete mixing and heat transfer in a very short time period. This time period may be less than 3 seconds. The resulting mixture has an appearance and consistency similar to that of milk, and it is poured into a canister as a casting process at ambient pressure, whereby the mixture is able to self level and solidify within the canister.

Since the Comparative Solid Stick Composition was made with the batch process, two additional solid stick formulations were made with the dual stream process (Inventive Example 1 and Inventive Example 2) to investigate the role that manufacturing process may have on a solid stick antiperspirant composition containing a surfactant. The surfactant was added to the batch tank for the hot process stream. As can be seen from the Table 3 below, the Currently Marketed Soft Solid was better than the Comparative Solid Stick (Batch, Surfactant), even though the Comparative Solid Stick contained a surfactant. The Currently Marketed Solid Stick (Stream, No Surfactant) was slightly better than the Comparative Solid Stick (Batch, Surfactant), which might be expected due to the slightly more efficacious antiperspirant active. Surprisingly, Inventive Example 1 (Stream, Surfactant) was significantly better than both the Comparative Solid Stick (Batch, Surfactant) and the Currently Marketed Solid Stick (Stream, No Surfactant) but still did not beat the Currently Marketed Soft Solid.

Most surprising, however, Inventive Example 2 was significantly better than the Currently Marketed Soft Solid, 62 mg better than the Currently Marketed Solid Stick (Stream, No Surfactant), and 50.5 mg better than Inventive Example 1. The magnitude of the improvement of (4× the number of mg improved) Inventive Example 2 over Inventive Example 1 is believed surprising given the only difference is the more efficacious active. Inventive Solid Stick Example 1 utilized aluminum zirconium trichlorohydrex while Inventive Formula 2 utilized aluminum zirconium tetrachlorohydrex. While aluminum zirconium tetrachlorohydrex actives are more acidic and can potentially provide an incremental efficacy boost, it is believed to be surprising to see this much of an additional boost in efficacy. While not wishing to be bound by theory, it is believed that the more hygroscopic nature of the aluminum zirconium tetrachlorohydrex active as compared to the utilized aluminum zirconium trichlorohydrex resulted in increased water transport through the water transport pathways created by the surfactant.

stream. The composition solidifies shortly thereafter in the canister all of which prevents the surfactant from having much access to the antiperspirant active, and thus less of an ability to bind to it, while still providing its originally desired benefit of aiding break-up the structurant to allow for better water transport into and out of the antiperspirant composition film during a sweat event.

Without intending to be bound by any theory, it is believed the amount of time the surfactant and antiperspirant active have to interact impacts their ability to bind and impacts the resulting efficacy of the solid stick antiperspirant composition. Thus, it is believed that if the contact time between the surfactant and antiperspirant active from the moment when the surfactant and the antiperspirant active are mixed to the moment when the mixture exits the nozzle and is poured into a canister can be limited to 5 minutes or less, binding to the antiperspirant active by the surfactant may be sufficiently minimized and the resulting solid stick antiperspirant composition will have an improved efficacy over its non-surfactant containing counterpart. Further minimizing this time period to 3 minutes or less; 1 minute or less; 30 seconds or less; 15 seconds or less; 5 seconds or less; or 3 seconds or less are also desirable.

One method known in the art for evaluating antiperspirant composition efficacy enhancement is the Red Dot method. This method looks at how water is transported into and then released from the antiperspirant composition film. This method is more particularly described in commonly assigned USPN 2005/0287069. So, for the biggest impact, there is a balance between how quickly water can get into the composition and how well it gets out. This is important because the effectiveness of an antiperspirant active is related to the transport of sweat (water) in and out of the

TABLE 3

| PRODUCT | SURFACTANT | PROCESS | Active/Metal-Chloride Ratio | RESULT COMPARED TO A STREAM SOLID STICK | RESULT COMPARED TO SOFT SOLID |
|---|---|---|---|---|---|
| Currently Marketed Soft Solid | No | Batch | Aluminum zirconium trichlorohydrex about 1.55 | NA | Benchmark |
| Comparative Solid Stick Composition | Yes | Batch | Aluminum zirconium trichlorohydrex about 1.55 | NA | 36 mg more sweat than Benchmark |
| Currently Marketed Solid Stick Composition | No | Stream | Aluminum zirconium tetrachlorohydrex about 1.2 | Benchmark | 33.5 mg more sweat than Benchmark |
| Inventive Solid Stick Example 1 | Yes | Stream | Aluminum zirconium trichlorohydrex about 1.55 | 11.5 mg less than Benchmark | 22 mg more sweat than Benchmark |
| Inventive Solid Stick Example 2 | Yes | Stream | Aluminum zirconium tetrachlorohydrex about 1.2 | 62 mg less than Benchmark | 28.5 mg less sweat than Benchmark |

Without intending to be limited by theory, it is believed that the surfactant likes to bind the antiperspirant active, thereby impeding both antiperspirant active effectiveness and the ability of the surfactant to create water transport pathways in the wax structure and allow for better water transport. Thus, in a single batch process where all of the ingredients are combined and mixed together for a significant amount of time in a molten solution, the surfactant has time to find and bind to the antiperspirant active which impedes its release. Conversely, in the dual stream method, the surfactant is in the hot stream with the structurant and only briefly mixes with the antiperspirant active in the cold composition film to solubilize the antiperspirant active and transport it back into the sweat duct to form a plug.

Anything that can impede transport can reduce the efficacy of an antiperspirant composition. For example, the Indicator solution would have a high a-value by itself without being neutralized by any acidic salts. Without intending to be bound by any theory, it is believed that a highly efficacious antiperspirant composition would have a relatively high a-value (e.g., greater than 1) after 30 seconds. This demonstrates that the antiperspirant composition film is not too hydrophilic, so that it does not immediately start interacting with the acidic pH of the antiperspirant active within the composition film. A lower value (below 1) indicates the product film is very hydrophilic, which like a large diameter (discussed below), can impede transport out of the antiperspirant composition film and reduce efficacy.

To ensure proper transport through the antiperspirant composition film, it may also be desirable to see a low a-value (e.g., below an a-value of 0.4) between 2, 3 and/or 4 minutes and 15 minutes. This shows that the composition film is capable of transporting the indicator efficiently to the active to be neutralized by the acidity of the antiperspirant active. This may be important because this indicates efficient transport into the antiperspirant composition film to solubilize the antiperspirant active. At this time point, the higher the a-value the less efficient the composition film is at transporting moisture to the antiperspirant active.

After 24 hours, it may be desirable to see the a-value increase back above about 1 or more. Without intending to be bound by any theory, a reading below this value may suggest the now acidic solution was not able to transport out of the antiperspirant composition film efficiently leaving some active trapped in the film and reducing the efficiency of transport during the next sweat event. Since a consumer may undergo multiple sweat events during the course of usage, it is desirable to ensure the antiperspirant composition film is efficient for transport during multiple sweat events, not just the first. It is believed that it may further be desirable for a solid stick antiperspirant composition to have the combination of the following: a) a relatively high a-value (e.g., greater than 1) after 30 seconds, b) a low a-value (e.g., below an a-value of 0.4) between 2, 3 and/or 4 minutes and 15 minutes and/or c) an a-value above about 1 or more after 24 hours.

Some Red Dot measurements for some currently marketed invisible solid stick compositions and the Inventive Solid Stick Composition Examples 2 and 3 are set forth below in Table 4. Comparing Inventive Solid Stick Example 2 to the two closest currently marketed invisible solid stick compositions tested, from a Red Dot Method measurement point of view, currently marketed IS #2 has such a low a-value after 30 seconds and such a large diameter that it suggests this composition film is very hydrophilic and that may negatively impact efficacy by impeding transport out of the composition film. And currently marketed IS #6 has a 24 hour average that is too low, which shows the composition film may not be efficient through multiple sweat events, resulting in lower efficacy due to the fact that a significant amount of the active was not able to transport out of the composition film, significantly reducing efficacy.

Currently Marketed IS #5 in Table 4 below is the same composition presented above in Table 2 as the Currently Marketed Solid Stick Composition. Interestingly, without intending to be bound by any theory, it is believed the dramatically increased efficacy, as shown in Table 2, of Inventive Solid Stick Example #2 compared to IS#5 may be further illustrated by the lower a-values between 2, 3 and/or 4 minutes and 15 minutes of Inventive Solid Stick Example #2. Inventive Solid Stick Example 3 also performed very well, although it had a higher red dot value at 3 minutes compared to Inventive Example 2, indicating a slightly lower initial water uptake, possibly due to the antiperspirant active (aluminum zirconium pentachlorohydrate glycine, metal:chloride ratio 1.55) being less hygroscopic than the aluminum zirconium tetrachlorohydrate glycine (metal:chloride ration 1.2) of Inventive Example 2. Without intending to be bound by any theory, it is believed that substituting, into Inventive Example 3, an aluminum zirconium pentachlorohydrate active having a metal:chloride ratio of 1.5 or less and/or adjusting the aluminum to zirconium ration downward (e.g., from 9 to 8.5) may improve the red dot value(s) of Inventive Example 3, possibly even close to those of Inventive Example 2.

TABLE 4

| Time | Current Market IS # 2 | Current Market IS # 3 | Current Market IS # 4 | Current Market IS # 5 | Current Market IS # 6 | Current Market IS # 7 | Inventive Solid Stick # 2 | Current Market IS # 8 | Current Market IS # 9 | Inventive Solid Stick #3 |
|---|---|---|---|---|---|---|---|---|---|---|
| 30 s avg | −0.28 | 2.61 | −0.37 | 1.75 | 1.79 | 2.77 | 1.80 | 1.62 | 2.10 | 2.11 |
| 2 min avg | −0.74 | 1.38 | −0.52 | 0.50 | 0.32 | 1.70 | 0.31 | 0.55 | 0.73 | 0.52 |
| 3 min avg | −0.87 | 1.02 | −0.38 | 0.32 | 0.14 | 1.45 | 0.28 | 0.70 | 0.59 | 0.14 |
| 4 min avg | −0.81 | 0.89 | −0.47 | 0.46 | 0.25 | 1.26 | 0.32 | 0.74 | 0.51 | 0.20 |
| 5 min avg | −0.75 | 0.96 | −0.62 | 0.47 | 0.18 | 1.09 | 0.23 | 0.68 | 0.58 | 0.13 |
| 10 min avg | −0.69 | 1.08 | −0.57 | 0.42 | 0.20 | 1.23 | 0.11 | 0.74 | 0.71 | 0.07 |
| 15 min avg | −0.66 | 0.96 | −0.56 | 0.57 | 0.07 | 1.24 | 0.18 | 0.74 | 0.64 | 0.06 |
| 2-15 min avg | −0.76 | 1.00 | −0.52 | 0.45 | 0.17 | 1.27 | 0.23 | 0.72 | 0.61 | 0.14 |
| 24 hr avg | 1.72 | 1.78 | 1.19 | 1.94 | 0.79 | 3.21 | 1.67 | 1.66 | 1.32 | 0.9 |

Another way to look at the results from the Red Dot Method is to measure the diameter of the spot created during the test. The diameter of the spot can show the interaction between sweat (indicator) and the antiperspirant composition film. Since the amount of indicator applied is controlled and constant, the diameter is an indirect measure of contact angle. Too small of a diameter indicates the antiperspirant composition film is much too hydrophobic, resulting in a large contact angle and small diameter. This indicates water will have a hard time transporting into the antiperspirant composition film, reducing efficacy. If the diameter is too large, it suggests the antiperspirant composition film itself is too hydrophilic resulting in a low contact angle. An antiperspirant composition film that is very hydrophilic may have high transport into the film, but low transport out of the film. Therefore, the ideal contact angle and diameter is one that is not too large and not too small. This will have the proper balance of maximizing transport into the antiperspirant composition film without hurting transport our of the composition film. Thus, a desirable diameter is thought to be from about 2 cm to about 3.5 cm. Red Dot Diameters for the compositions of Table 4 are set forth below in Table 5.

TABLE 5

| Currently Marketed IS # 2 | Currently Marketed IS # 3 | Currently Marketed IS # 4 | Currently Marketed IS # 5 | Currently Marketed IS # 6 | Currently Marketed IS # 7 | Inventive Solid Stick Composition # 2 | Currently Marketed IS # 8 | Currently Marketed IS # 9 |
|---|---|---|---|---|---|---|---|---|
| 4.06 | 1.97 | 2.81 | 2.19 | 2.79 | 2.20 | 2.89 | 3.05 | 2.14 |

The antiperspirant compositions may have a-values as measured according to the Red Dot Method described hereafter. The Red Dot a-value measurements are generally taken at 30 seconds; 2 minutes; 3 minutes; 4 minutes; 5 minutes; 10 minutes; 15 minutes; and 24 hours. In some embodiments, the composition may have a color a-value at 30 seconds from about 1, about 1.25, or from about 1.5; to about 3; or about 4. A color a-value at time points 2 minutes; 3 minutes; 4 minutes; 5 minutes; 10 minutes; and 15 minutes can be, for example, 0.4 or less at each time point. Additionally, the a-values at each of time points 2 minutes; 3 minutes; 4 minutes; 5 minutes; 10 minutes; and 15 minutes can be averaged and then the value can be, for example, about 0.5 or less or about 0.4 or less. A color a-value at 24 hours can be, for example, about 0.75 or more; about 1 or more; about 1.25 or more; or about 1.5 or more; to about 3 or less; or about 4 or less. A 24 diameter reading can be, for example, from about 2.0; about 2.25; or about 2.5; to about 3.5; or about 3.25.

III. Solid Stick Antiperspirant Compositions

Solid stick antiperspirant compositions contain an antiperspirant active, one or more structurants, which may in some instances include one or more waxes, and a surfactant. The solid stick antiperspirant compositions are preferably anhydrous. The compositions may also comprise an anhydrous liquid carrier and other components as described below. The antiperspirant compositions are a single phase meaning the final composition is homogenous with respect to active distribution, wax and surfactant concentration. They are not macroscopically segregated by a physical separation into distinct regions of 3D space which could allow for some heterogeneity across the composition. The liquids also do not contain a dispersed liquid phase, microscopically separated such as in an emulsion (water in oil or oil in water). Solids stick antiperspirant compositions typically have a hardness of about 600 gram force or more before dispensing (compared to soft solid antiperspirant compositions which may have a hardness of 400 gram force or less). Hardness can be measured in accordance with the Antiperspirant Hardness method described below.

Antiperspirant Actives

The solid stick antiperspirant compositions comprise an antiperspirant active suitable for application to human skin. The concentration of the antiperspirant active in the composition should be sufficient to provide the desired enhanced wetness protection. For example, the active may be present in an amount of from about 0.1%, about 0.5%, about 1%, or about 5%; to about 60%, about 35%, about 25% or about 20%, by weight of the composition. These weight percentages are calculated on an anhydrous metal salt basis exclusive of water and any complexing agents such as glycine, glycine salts, or other complexing agents and may be calculated by taking the total active raw material level and multiplying it by the anhydrous assay of the active as determined by the USP method for assay determination (e.g., United States Pharmacopeia 37-National Formulary 32), as commonly known in the art. The preferred antiperspirant active are particulate antiperspirant materials preferably have average particle sizes of less than about 125 microns and more preferably less than 30 micron, or 20 micron or 10 microns.

An antiperspirant active can include any compound, composition, or other material having antiperspirant activity and which has a hygroscopicity greater than 30%. In some instances, the antiperspirant active may also have a metal to chloride ratio less than 1.5, as measured according to United States Pharmacopeia 37-National Formulary 32, for antiperspirant actives.

1. Hygroscopicity

One way to evaluate the hygroscopic nature of an antiperspirant active is to determine the equilibrium moisture pick up of the active after 5 days in a controlled relative humidity environment. Specific humidity chambers can be created placing saturated salt solutions in desiccators at a specific temperature. Different salts are used to create different humidities, for example potassium chloride can be used to make an 86% relative humidity (RH) environment at 20° C. An example of moisture pick up at a variety of relative humidities is shown in FIG. 1. In general there is an increase in moisture pick up as humidity is increased for the antiperspirant actives shown, however there are clear differences in slope and amount of moisture pick up at high humidity. Materials with higher slope and larger increases at high humidity (i.e. 86% RH) are considered to be more hygroscopic. The aluminum zirconium trichlorohydrate active (metal to chloride ratio=1.6) from Inventive Example 1 is the least hygroscopic (28% moisture pick up at 86% RH) with the aluminum zirconium tetrachlorohydrate active (metal to chloride ratio=1.2) being substantially more hygroscopic (40% moisture pick up at 86% RH). It is believed that antiperspirant actives with more than 30% moisture pick up at 86% humidity are more capable of pulling water through the water transport pathways created by the surfactant in wax matrix, thereby enhancing active transport to the sweat duct and creating enhanced sweat reduction. This may explain the substantial difference observed in the amount of sweat measured between Inventive Examples 1 and 2. One method for measuring hygroscopicity is described hereafter.

The hygroscopicity of an active is a function of its composition, and method of manufacturing but generally increases with increased acidity (i.e. lower metal to chloride ratio) and the presence of zirconium in the active (lower aluminum to zirconium ratios). In some embodiments, the antiperspirant active has a hygroscopicity from about 30%, 32%, 34%, 36%, 38% or 40% to about 60%, 55%, 50%, 48%, 46% or 44% after 5 days in a controlled relative humidity environment held at 86% relative humidity. In some instances, the hygroscopicity may be from 30% to 36% or 46% to 60% after 5 days in a controlled relative humidity environment held at 86% relative humidity, 2. Acidity Generally, more acidic antiperspirant actives are believed to more efficacious, in part due to a higher level of hygroscopicity arising from more acidic actives. Acidity of an antiperspirant active is a function of it composition specifically, the presence and level of zirconium (a proxy for this being the aluminum to zirconium ratio of the active) and the metal to chloride ratio of the active. Within actives without zirconium, aluminum sequichlorohydrate (Metal:Chloride ratio of 1.26-1.9) is more typically acidic than aluminum chlorohydrate (Metal:Chloride ratio of 1.9-2.0). The addition of zirconium generally creates a more acidic active than an aluminum only active with a similar metal to chloride ratio. Within aluminum zirconium salts such as aluminum zirconium trichlorohydrate glycine (Metal:Chloride ratio of 1.51-2.1), aluminum zirconium tetrachlorohydrate glycine (Metal:Chloride ratio of 0.9-1.5), aluminum zirconium pentachlorodrate glycine (Metal:Chloride ratio of 1.51-2.1), and aluminum zirconium octachlorohydrate glycine (Metal:Chloride ratio of 0.9-1.5), there is also generally an increase in acid with reduction in metal to chloride ratio. However, processing methods such as order of addition, heating, choice of raw material may also impact acidity and hygroscopicity. For many antiperspirant actives containing a zirconium salt, it is believed that a metal to chloride ratio from about 0.9, 1, 1.1, 1.2, 1.3, 1.4 or 1.45 to about 1.5, 1.4, 1.3 or 1.2 (or less than about 1.5, 1.4 or 1.3) is desirable if the antiperspirant active has a hygroscopicity from (or greater than) 30%, 32%, 34%, 36%, 38%, 40% or 50% or to 60% at 86% relative humidity at 5 days. In some instances, the antiperspirant active may have a metal to chloride ratio from 1.3 or 1.35 or 1.4 to 1.5 or 1.55, or the antiperspirant active may have a metal to chloride ratio from 0.9 to 1.1 or 1.15 in combination with a hygroscopicity of 30%, 32%, 34%, 36%, 38%, 40%, 50% or 60% at 86% relative humidity at 5 days. In some other instances, it may be desirable for an antiperspirant active containing a zirconium salt to have a metal to chloride ratio from (or greater than) 1.3, 1.35, 1.4, 1.45 or 1.5 to 1.6 or 1.5 in combination with a hygroscopicity from (or greater than) 30%, 32%, 34%, 36%, 38% or 40% to 60% at a relative humidity of 86% at 5 days. One example of such an antiperspirant active is aluminum zirconium pentachlorohydrate glycine, which may have a metal to chloride ratio in some instances of 1.5 or 1.55 (see, e.g., FIG. 1). In combination with the metal to chloride ratios described above, the antiperspirant actives may, in some instances, have an aluminum to zirconium ratios from about 3 to about 5.5.

3. Aluminum Salts

Aluminum salts useful herein can include those that conform to the formula:

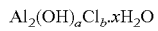

wherein a is from about 2 to about 5; the sum of a and b is about 6; x is from about 1 to about 6; where a, b, and x may have non-integer values. For example, aluminum chlorohydroxides referred to as "5/6 basic chlorohydroxide" or aluminum chlorohydrate wherein a is about 5 and "2/3 basic chlorohydroxide" or aluminum sequichlorohydrate, wherein a=4 may be used.

A general description of these aluminum salts can be found in *Antiperspirants and Deodorants*, Cosmetic Science and Technology Series Vol. 20, 2nd edition, edited by Karl Laden. Mixtures of aluminum salts are described in British Patent Specification 1,347,950, filed in the name of Shin et al. and published Feb. 24, 1974.

4. Zirconium Salts

Zirconium salts useful herein can include those which conform to the formula:

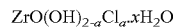

wherein a is from about 1.5 to about 1.87; x is from about 1 to about 7; and wherein a and x may both have non-integer values. These zirconium salts are described in Belgian Patent 825,146, issued to Schmitz on Aug. 4, 1975. Some examples of preferred salts are described in U.S. Pat. No. 4,775,528A. Useful to the present invention are zirconium salt complexes that additionally contain aluminum and glycine, commonly known as "ZAG complexes". These complexes can contain aluminum chlorohydroxide and zirconyl hydroxy chloride conforming to the above-described formulas. Some examples of complexes include aluminum zirconium trichlorohydrex, aluminum zirconium tetrachlorohydrex, aluminum zirconium pentachlorodrex, aluminum zirconium octachlorohydrex, aluminum zirconium trichlorohydrate glycine, aluminum zirconium tetrachlorohydrate glycine, aluminum zirconium pentachlorodrate glycine, and aluminum zirconium octachlorohydrate glycine. One skilled in the art will find methods for characterizing elemental composition, metal to chloride ratio and Aluminum to zirconium ratio in the United States Pharmacopeia Vol 37-National Formulary Vol 32.

Antiperspirant actives containing both aluminum and zirconium are preferred over aluminum only actives. One preferred active is aluminum zirconium tetrachlorohydrate glycine comprising a metal to chloride molar ratio of less than or equal to about 1.4. Preferably, the metal to chloride molar ratio is from about 1.3 to about 0.9, and more preferably, the ratio is about 1.25. A particular preferred zirconium tetrachlorohydrate glycine active would have a metal to chloride ratio of 0.9 to 1.3 and an aluminum to zirconium mole ratio of 3 to 5.5 with a hygroscopicity of more than 35%. Another preferred material is aluminum zirconium pentachlorohydrate glycine having a metal to chloride ratio of 1.5 to 1.8, more preferable about 1.55. A particular preferred zirconium pentachlorohydrate glycine active would have a metal to chloride ratio of 1.5 to 1.7 and an aluminum to zirconium mole ratio of 8.5 to 10 with a hygroscopicity of more than 35%. In some instances, the solid stick antiperspirant composition may be substantially or completely free of aluminum zirconium tetrachlorohydrate glycine having a metal to chloride ratio from 1.2 to 1.3. In some other instances, the solid stick antiperspirant composition is substantially or completely free of aluminum zirconium trichlorohydrex, and/or aluminum zirconium trichlorohydrate glycine having a metal to chloride ratio less than 1.3. In some instances, the antiperspirant active may have a metal to chloride ratio greater than 1.4.

Structurants

The antiperspirant compositions also comprise one or more structurants to provide the solid stick antiperspirant composition with the desired viscosity, rheology, texture and/or hardness, or to otherwise help suspend any dispersed solids or liquids within the antiperspirant composition. The one or more structurants comprise at least one wax. The term "structurant" may also include any hydrophobic material known or otherwise effective in providing suspending, gelling, viscosifying, solidifying, or thickening properties to the composition or which otherwise provide structure to the solid stick antiperspirant composition. These structurants may include, for example, gelling agents, polymeric or nonpolymeric agents, inorganic thickening agents, or viscosifying agents. The thickening agents may include, for example, organic solids, silicone solids, crystalline or other gellants, inorganic particulates such as clays or silicas, or combinations thereof.

Waxes may be natural or synthetic materials. In some instances, one or more (or all) of the waxes present in the solid stick antiperspirant composition have a melt temperature less than about 90° C. 85° C., 80° C. 75° C. 70° C. or 60° C. Some examples include natural vegetable waxes such as, for example, candelilla wax, carnauba wax, Japan wax, espartograss wax, cork wax, guaruma wax, rice oil wax, sugar cane wax, ouricury wax, montan wax, sunflower wax, fruit waxes, such as orange waxes, lemon waxes, grapefruit wax, bayberry wax, and animal waxes such as, for example, beeswax, shellac wax, spermaceti, wool wax and uropygial fat. Natural waxes may include the mineral waxes, such as ceresine and ozocerite for example, or the petrochemical waxes, for example petrolatum, paraffin waxes and microwaxes. Chemically modified waxes may be used, such as, for example, montan ester waxes, sasol waxes and hydrogenated jojoba waxes. Synthetic waxes include, for example, a polyethylene, a polymethylene, or a combination thereof.

The wax may also be selected from the group of esters of saturated and/or unsaturated, branched and/or unbranched alkanecarboxylic acids and saturated and/or unsaturated, branched and/or unbranched alcohols, from the group of esters of aromatic carboxylic acids, dicarboxylic acids, tricarboxylic acids and hydroxycarboxylic acids (for example 12-hydroxystearic acid) and saturated and/or unsaturated, branched and/or unbranched alcohols and also from the group of lactides of long-chain hydroxycarboxylic acids. Wax components such as these include, for example, C16-40 alkyl stearates, C20-40 alkyl stearates (for example Kesterwachs (Registered trademark K82H), C20-40 dialkyl esters of dimer acids, C18-38 alkyl hydroxystearoyl stearates or C20-40 alkyl erucates. Other suitable waxes which may be used include C30-50 alkyl beeswax, tristearyl citrate, triisostearyl citrate, stearyl heptanoate, stearyl octanoate, trilauryl citrate, ethylene glycol dipalmitate, ethylene glycol distearate, ethylene glycol di(12-hydroxystearate), stearyl stearate, palmityl stearate, stearyl behenate, cetyl ester, cetearyl behenate and behenyl behenate. Silicone waxes may also be used.

Some preferred examples of acceptable non-polar waxes include glyceryl tribehenate, polyethylene, polymethylene (e.g., Accumelt 68 and 78 available from International Group, Inc., USA), $C_{18}$-$C_{36}$ triglyceride (e.g., Synchrowax HGL-C available from Croda, Inc., USA), hydrogenated high euricic aid rapeseed oil (hear stearine), ozokerite and combinations thereof. Some preferred examples of acceptable polar waxes include stearyl alcohol, hydrogenated castor oil, myristyl alcohol, cetyl alcohol, and combinations thereof. The wax may comprise a blend of polar and non-polar waxes. For example, a combination of polar and non-polar waxes may be selected from the list above. In some instances, the wax may have a melt point above 65° C., more typically from about 65° C. to about 130° C. Some suitable polymethylenes may have a melting point from about 65° C. to about 75° C. Examples of suitable polyethylenes include those with a melting point from about 60° C. to about 95° C. Other high melting point waxes are described in U.S. Pat. No. 4,049,792, Elsnau, issued Sep. 20, 1977. Solid stick antiperspirant composition may have a total wax concentration from about 10%, 12%, or 14% to about 25%, 20%, 18% or 16% by weight of the antiperspirant composition. It is believed that the surfactant addition described herein is particularly beneficial for structurant levels greater than 10% as these higher levels are more likely to create more of a hydrophobic barrier to water transport which may be seen in solid stick antiperspirant compositions.

The antiperspirant compositions may also comprise one or more structurants other than wax. For example, one or more gelling agents may be included. Some non-limiting examples of suitable gelling agents include fatty acid gellants, salts of fatty acids, hydroxyl acids, hydroxyl acid gellants, esters and amides of fatty acid or hydroxyl fatty acid gellants, cholesterolic materials, dibenzylidene alditols, lanolinolic materials, fatty alcohols, triglycerides, sucrose esters such as SEFA behenate, inorganic materials such as clays or silicas, other amide or polyamide gellants, and mixtures thereof.

Suitable gelling agents include fatty acid gellants such as fatty acid and hydroxyl or alpha hydroxyl fatty acids, having from about 10 to about 40 carbon atoms, and ester and amides of such gelling agents. Non-limiting examples of such gelling agents include, but are not limited to, 12-hydroxystearic acid, 12-hydroxylauric acid, 16-hydroxyhexadecanoic acid, behenic acid, eurcic acid, stearic acid, caprylic acid, lauric acid, isostearic acid, and combinations thereof. Preferred gelling agents are 12-hydroxystearic acid, esters of 12-hydroxystearic acid, amides of 12-hydroxystearic acid and combinations thereof.

Other suitable gelling agents include amide gellants such as di-substituted or branched monoamide gellants, monosubstituted or branched diamide gellants, triamide gellants, and combinations thereof, including n-acyl amino acid derivatives such as n-acyl amino acid amides, n-acyl amino acid esters prepared from glutamic acid, lysine, glutamine, aspartic acid, and combinations thereof. Other suitable amide gelling agents are described in U.S. Pat. No. 5,429,816, issued Jul. 4, 1995, and U.S. Pat. No. 5,840,287, filed Dec. 20, 1996.

Still other examples of suitable gelling agents include fatty alcohols having at least about 8 carbon atoms, at least about 12 carbon atoms but no more than about 40 carbon atoms, no more than about 30 carbon atoms, or no more than about 18 carbon atoms. For example, fatty alcohols include but are not limited to cetyl alcohol, myristyl alcohol, stearyl alcohol and combinations thereof.

Non limiting examples of suitable triglyceride gellants include tristearin, hydrogenated vegetable oil, trihydroxystearin (Thixcin® R, available from Rheox, Inc.), rape seed oil, castor wax, fish oils, tripalmitin, Syncrowax® HRC and Syncrowax® HGL-C (Syncrowax® available from Croda, Inc.).

Some other structurants for use in the solid stick antiperspirant compositions may include inorganic particulate thickening agents such as clays and colloidal pyrogenic silica pigments. For example, colloidal pyrogenic silica pigments such as Cab-O—Sil®, a submicroscopic particulated pyrogenic silica may be used. Other known or otherwise effective inorganic particulate thickening agents that are commonly used in the art can also be used in the solid antiperspirant compositions of the present invention. Concentrations of particulate thickening agents may range, for example, from about 0.1%, about 1%, or about 5%; to about 35%, about 15%, about 10% or about 8%, by weight of the composition.

Suitable clay structurants include montmorillonite clays, examples of which include bentonites, hectorites, and colloidal magnesium aluminum silicates. These and other suitable clays may be hydrophobically treated, and when so treated will generally be used in combination with a clay activator. Non-limiting examples of suitable clay activators include propylene carbonate, ethanol, and combinations thereof. When clay activators are present, the amount of clay activator will typically range from about 40%, about 25%, or about 15%; to about 75%, about 60%, or about 50%, by weight of the clay.

A solid stick antiperspirant composition may contain from about 15% to about 25%, by weight of the antiperspirant composition, of structurants.

Surfactants

The antiperspirant compositions also comprise one or more solid surfactants at room temperature. A surfactant is generally present at a level of about 0.05% to about 5%, by weight of the antiperspirant composition, but may contain, from about 0.5% to about 5%; from about 1% to about 4%; from about 1.5% to about 3.5%; from about 1.75% to about 2.5%; about 2%, or any combination thereof. The surfactant can have a HLB (hydrophilic-lipohilic balance) range of about 2 to about 14; about 6 to about 12; about 8 to about 10; or any combination thereof. Without intending to be bound by any theory, it is believed that the range from about 6 to about 12 is most preferred, as it is believed to strike a preferred balance between being hydrophilic enough to create the desired water transport routes while still being lipophilic enough to enough to crystallize in the hydrophobic wax phase. The surfactant can be any known in the art, including nonionic, cationic and anionic. Nonionic and cationic are preferred as they are less likely to interact with the antiperspirant active. Nonionic are most preferred as they will not alter the plugging process of the active via a pH change. Further solid surfactants are preferred to liquid as it is believed they are more likely to remain in the wax after crystallization and thereby create the desired water transport pathways. Moreover, surfactants with a melt points greater than 40° C. are preferred as it is believed that they will co-crystallize with the structurant and thereby create the desired water transport pathways. Surfactants with melts points higher than 50° C., or 60° C. or 70° C. or 80° C. are more preferred. In some instances, the melt temperature of the surfactant may be from 50° C., 60° C., 70° C. or 80° C. to 120° C., 110° C., 100° C. or 90° C. The melt temperature may be measure using USP method 741 or other methods as known in the art. Preferably, the surfactant has a melt temperature that is greater than the crystallization onset temperature of the solid stick antiperspirant composition. The antiperspirant active and the surfactant are in contact for about 5 minutes or less from the moment that the antiperspirant active and the surfactant and the structurant are mixed until the moment that the mixture is dispensed from the nozzle.

One class of preferred nonionic surfactants include ethoxylated fatty acid esters or fatty alcohol ethers. Fatty acid or alcohol chain lengths can vary from about 16 to about 50 carbons. Generally, longer linear chain lengths will increase the melt temperature of the surfactant, with linear chain lengths greater than 20 being preferred. Branched chains may tend to reduce the melt temperature of the surfactant and are therefore less preferred. Ethoxylate chain lengths for these fatty acid esters can vary from about 1 to about 100 to provide the desired HLB. Examples of these include but are not limited to steareth-2, steareth-20, steareth-100, ceteareth-20, ceteth-20, $C_{20-40}$ Pareth-3, $C_{20-40}$ Pareth-40, $C_{30-50}$ Pareth-10. One preferred surfactant may comprise, for example, a $C_{20-40}$ Pareth-10. Another suitable surfactant is a nonionic ethoxylated linear alcohol with a carbon chain length of 20-40. One specific example of a suitable surfactant includes PERFORMATHOX™ 450 ethoxylate, which has a melt temperature of 90° C. The surfactant may be free of polyoxyethylene sorbitan fatty acids.

Anhydrous Liquid Carriers

The antiperspirant compositions further comprise one or more anhydrous liquid carriers. These are present, for example, at concentrations ranging from about 10%, about 15%, about 20%, about 25%; to about 99%, about 70%, about 60%, or about 50%, by weight of the antiperspirant composition. Such concentrations will vary depending upon variables such as composition form, desired composition hardness, and selection of other ingredients in the composition. The anhydrous carrier may be any anhydrous carrier known for use in personal care applications or otherwise suitable for topical application to the skin. For example, anhydrous carriers may include, but are not limited to volatile and nonvolatile fluids and combinations thereof.

A. Volatile Fluids

A solid stick antiperspirant composition may further comprise a volatile fluid, such as a volatile silicone fluid. Volatile fluids are present, for example, at concentrations ranging from about 20% or from about 30%; to about 80%, or no about 60%, by weight of the composition. The volatile silicone of the solvent may be cyclic, linear, and/or branched chain silicone. "Volatile silicone", as used herein, refers to those silicone materials that have measurable vapor pressure under ambient conditions. Non-limiting examples of suitable volatile silicones are described in Todd et al., "Volatile Silicone Fluids for Cosmetics", Cosmetics and Toiletries, 91:27-32 (1976).

The volatile silicone may be a cyclic silicone. The cyclic silicone may have from about 3 silicone atoms, or from about 5 silicone atoms; to about 7 silicone atoms, or about 6 silicone atoms. For example, volatile silicones may be used which conform to the formula:

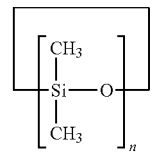

wherein n is from about 3, or from about 5; to about 7, or about 6. These volatile cyclic silicones generally have a viscosity of less than about 10 centistokes at 25° C. Suitable volatile silicones for use herein include, but are not limited to, Cyclomethicone D5 (commercially available from G. E. Silicones); Dow Corning 344, and Dow Corning 345 (commercially available from Dow Corning Corp.); and GE 7207, GE 7158 and Silicone Fluids SF-1202 and SF-1173 (available from General Electric Co.). SWS-03314, SWS-03400, F-222, F-223, F-250, F-251 (available from SWS Silicones Corp.); Volatile Silicones 7158, 7207, 7349 (available from Union Carbide); Masil SF-V (available from Mazer) and combinations thereof.

B. Non-Volatile Fluids

The non-volatile organic fluid can be present, for example, at concentrations ranging from about 1%, from about 2%; to about 20%, or about 15%, by weight of the composition.

1. Non-Volatile Organic Fluids

The non-volatile organic fluid can be present at concentrations ranging from about 1%, from about 2% but no more than about 20% or no more than about 15%, by weight of the composition.

Non-limiting examples of nonvolatile organic fluids include, but are not limited to, mineral oil, PPG-14 butyl ether, isopropyl myristate, petrolatum, butyl stearate, cetyl octanoate, butyl myristate, myristyl myristate, C12-15 alkylbenzoate (e.g., Finsolv™), dipropylene glycol dibenzoate, PPG-15 stearyl ether benzoate and blends thereof (e.g. Finsolv TPP), neopentyl glycol diheptanoate (e.g. Lexfeel 7 supplied by Inolex), octyldodecanol, isostearyl isostearate, octododecyl benzoate, isostearyl lactate, isostearyl palmitate, isononyl/isononoate, isoeicosane, octyldodecyl neopentanate, hydrogenated polyisobutene, and isobutyl stearate. Many such other carrier liquids are disclosed in U.S. Pat. No. 6,013,248 (Luebbe et al.) and U.S. Pat. No. 5,968,489 (Swaile et al).

2. Non-Volatile Silicone Fluids

The antiperspirant composition may further comprise a non-volatile silicone fluid. The non-volatile silicone fluid may be a liquid at or below human skin temperature, or otherwise in liquid form within the anhydrous antiperspirant composition during or shortly after topical application. The concentration of the non-volatile silicone may be from about 1%, from about 2%; to about 15%, about 10%, by weight of the composition. Non-volatile silicone fluids may include those which conform to the formula:

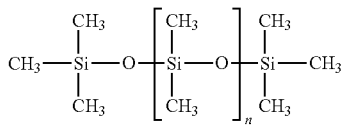

wherein n is greater than or equal to 1. These linear silicone materials may generally have viscosity values of from about 5 centistokes, from about 10 centistokes; to about 100,000 centistokes, about 500 centistokes, about 200 centistokes, or about 50 centistokes, as measured under ambient conditions.

Specific non limiting examples of suitable nonvolatile silicone fluids include Dow Corning 200, hexamethyldisiloxane, Dow Corning 225, Dow Corning 1732, Dow Corning 5732, Dow Corning 5750 (available from Dow Corning Corp.); and SF-96, SF-1066 and SF18(350) Silicone Fluids (available from G.E. Silicones).

Low surface tension non-volatile solvent may be also be used. Such solvents may be selected from the group consisting of dimethicones, dimethicone copolyols, phenyl trimethicones, alkyl dimethicones, alkyl methicones, and mixtures thereof. Low surface tension non-volatile solvents are also described in U.S. Pat. No. 6,835,373 (Kolodzik et al.).

Malodor Reducing Agents

The solid stick antiperspirant composition may optionally comprise a malodor reducing agent. Malodor reducing agents include components other than the antiperspirant active within the composition that act to eliminate the effect that body odor has on fragrance display. These agents may combine with the offensive body odor so that they are not detectable including, but not limited to, suppressing evaporation of malodor from the body, absorbing sweat or malodor, masking the malodor or microbiological activity on odor causing organisms. The concentration of the malodor reducing agent within the composition is sufficient to provide such chemical or biological means for reducing or eliminating body odor. Although the concentration will vary depending on the agent used, generally, the malodor reducing agent may be included within the composition from about 0.05%, about 0.5%, or about 1%; to about 15%, about 10%, or about 6%, by weight of the composition.

Malodor reducing agents may include, but are not limited to, pantothenic acid and its derivatives, petrolatum, menthyl acetate, uncomplexed cyclodextrins and derivatives thereof, talc, silica and mixtures thereof. Such agents may be used as described in U.S. Pat. No. 6,495,149, issued to Scavone, et al and US patent application 2003/0152539, filed Jan. 25, 2002 in the names of Scavone, et al.

For example, if panthenyl triacetate is used, the concentration of the malodor reducing agent may be from about 0.1% or about 0.25%; to about 3%, or about 2%, by weight of the composition. Another example of a malodor reducing agent is petrolatum which may be included from about 0.10%, or about 0.5%; to about 15%, or about 10%, by weight of the composition. A combination may also be used as the malodor reducing agent including, but not limited to, panthenyl triacetate and petrolatum at levels from about 0.1%, or 0.5%; to about 3%, or about 10%, by weight of the composition. Menthyl acetate, a derivative of menthol that does not have a cooling effect, may be included from about 0.05%, or 0.01%; to about 2%, or about 1%, by weight of the composition. The malodor reducing agent of the present invention may be in the form of a liquid or a semi-solid such that it does not contribute to product residue.

IV. Dispensing Packages

The solid stick antiperspirant compositions described herein are stored within a dispensing packaging. A wide variety of dispensing packages may be utilized for dispensing the antiperspirant compositions described herein. The dispensing package typically has an open end through which the solid stick antiperspirant composition is dispensed.

Figure 2:
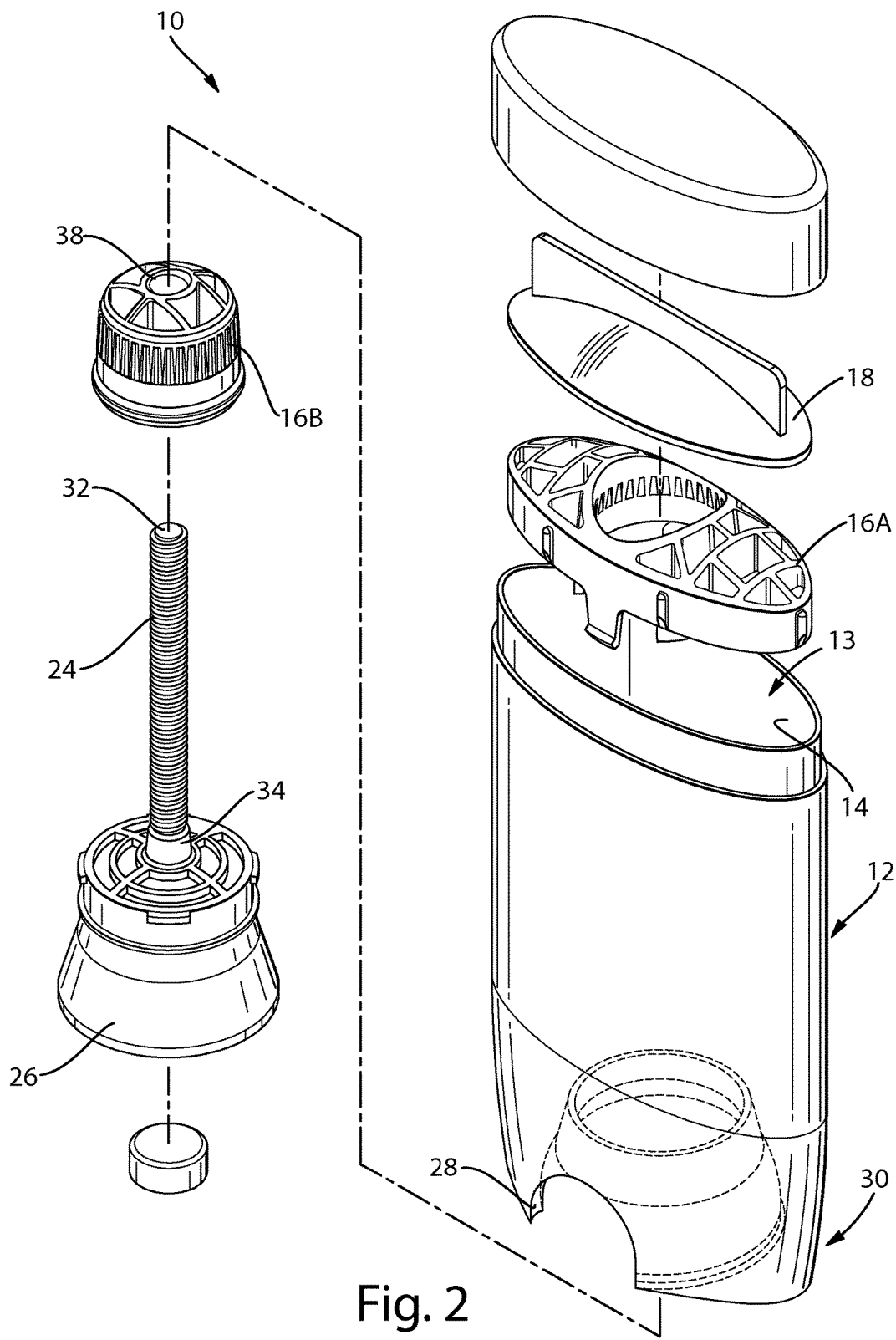
FIG. 2 is a perspective view of one non-limiting example of a dispensing package suitable for use with solid stick type antiperspirant compositions.

A wide variety of dispensing packages may also be utilized to dispense a solid stick antiperspirant composition. Some non-limiting examples are described in U.S. Pat. Nos. 5,401,112; 5,735,212; 8,187,578; and 2013/0170886. Referring now to FIG. 2, one example of a dispensing package 10 suitable for dispensing a solid stick antiperspirant composition is shown. The dispensing package 10 comprises a container body 12 having an open end 13, an interior chamber 14 and an elevator 16 slidably disposed within the interior chamber. In this particular embodiment, the elevator 16 comprises components 16A and 16B, although a single piece elevator that combines 16A and 16B may be substituted. A seal 18 may seal the open end 13 prior to first use by a consumer. A means for axially advancing the elevator 16 toward the open end 13 is also provided. Such means are well known in the packaging and antiperspirant art and may comprise a feed screw 24 or other similar functioning mechanisms which drive the elevator 16 in an axial direction toward the open end 13. The elevator 16 typically represents the bottom of the dispensing package on or above which the antiperspirant composition rests prior to dispensing. A feed screw 24 also disposed at least partially within the interior chamber 14. Hand wheel 26 is attached to the feed screw 24 for rotating the feed screw and thereby axially advancing the elevator 16 within the interior chamber 14 toward open end 13. The open end 13 is preferably congruent in shape and/or size with the with the shape and/or size of the interior chamber 14 so that the solid stick antiperspirant composition is advanced through the open end 13 without significant shearing or distortion of the antiperspirant stick composition.

Briefly, the threaded feed screw 24 may be actuated by rotating a hand wheel 26 or other mechanism coupled to the feed screw 24. In use, the hand wheel 26 is rotated, thereby rotating the feed screw 24. Since the elevator 16 is housed within the container body 12, rotation of the feed screw 24 causes the elevator 16 to move up the feed screw 24. The hand wheel 26 is held within a recess 28 formed externally of a second end 30 of the container body 12. The recess 28 is formed to house the hand wheel 26 therein, while permitting a user to engage and rotate the hand wheel 26 when the user desires to dispense the antiperspirant composition.

The feed screw 24 has a first end 32 and a second end 34 coupled to the hand wheel 26. In this way, the feed screw 24 is rotated when the hand wheel 26 is rotated by a user. The first end 32 of the feed screw 24 extends within the container body 12 such that the elevator 16 may ride on the feed screw 24 until it reaches a desired position adjacent the open end 13 of the container body 16. The elevator 16 includes a threaded central opening 38 shaped and sized to receive the feed screw 24.

V. Methods of Manufacturing

While a dual stream manufacturing method is described hereafter by way of example and not limitation, it will be appreciated that other manufacturing processes which minimize the contact time of the antiperspirant active and surfactant to less than 5 minutes prior to dispensing into dispensing package may also be used.

Figure 3:
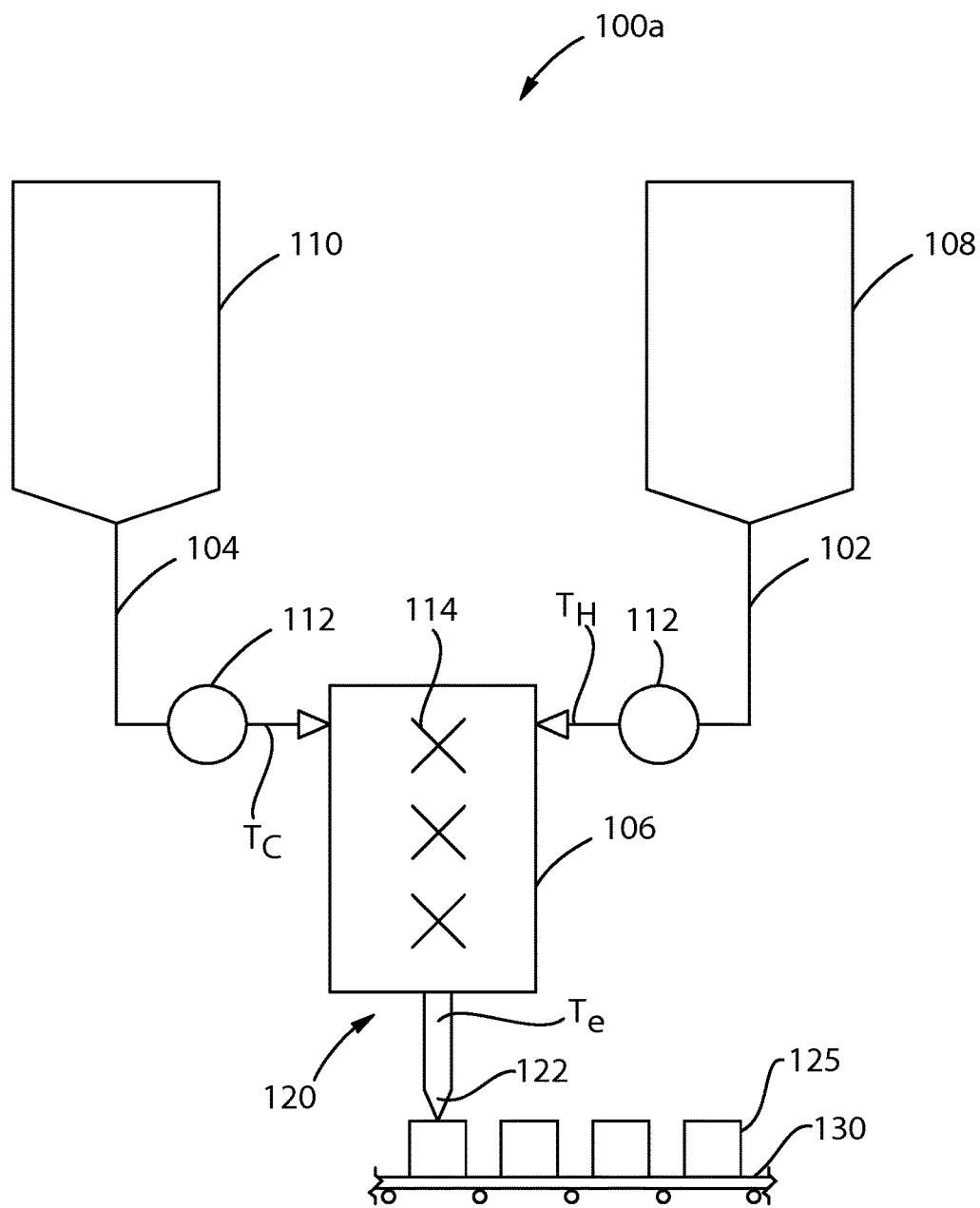
FIG. 3 is a schematic diagram of one non-limiting example of a dual stream manufacturing process for solid stick antiperspirant compositions.

Referring to FIG. 3, one example of a suitable manufacturing method is shown. The method 100 combines at least two process streams, a first stream 102 having a first temperature and second stream 104 having a second temperature lower than the first temperature, within a mixing chamber 106. Due to the differences in temperature, the first stream 102 may also be referred to as the hot stream, while the second stream 104 may be referred to as the cold stream. In FIG. 3, the first stream ingredients are mixed in a batch tank 108 while the second stream ingredients are mixed in separate batch tank 110. Conventional equipment, such as, for example, pumps 112 can be used to facilitate movement of the first and second streams 102, 104 towards and into a mixing chamber 106.

The first process stream 102 may contain, for example, one or more structurants (e.g., a wax) melted in a solvent, and a surfactant which are held above the full melting point of the one or more waxes. The solvent of the first process stream 102 may be any material that is liquid at the holding temperature of the hot process stream 102 and that can essentially completely dissolve the wax structurant. The solvent may be selected from any of the previously described liquid carriers. In some instances, the solvent comprises a silicone fluid, such as cyclomethicone and/or dimethicone (also referred to as polydimethylsiloxane).

The first process stream 102 is preferably heated to a temperature sufficient to melt the one or more waxes in the solvent. In some embodiments, the temperature of the first process stream 102 is from about 65° C., 70° C., 75° C. or 80° C. to about 130° C., 120° C., 110° C., 100° C. or 90° C. within the tank 108 or a static mixer used to combine the ingredients of the hot process stream 102. In some instances where the waxes are selected from the group consisting of stearyl alcohol, hydrogenated castor oil, ozokerite, synthetic wax, tribehenin, or C18-36 triglyceride and mixtures thereof, the temperature of the first stream composition within the tank 108 (or static mixer), is from about 75° C. to about 95° C. or from about 80° C. to about 95° C.

A second process stream 104 may contain the balance of the liquid carriers, an antiperspirant active and any heat-sensitive components. The step of forming a cold process stream can involve mixing an antiperspirant active, as described herein, and a solvent and optionally a heat sensitive component in the second batch tank 110 or a static mixer. The cold stream 104 has a second temperature $T_c$ that is lower than the temperature $T_h$. Preferably, the second batch tank and the temperature $T_c$ are at ambient, although it may be provided at other temperatures such as at least about 20, 50 or 70° C. lower than the temperature $T_h$. In instances where the waxes incorporated into the hot process stream are selected from the group consisting of stearyl alcohol, hydrogenated castor oil, ozokerite, and mixtures thereof, the temperature of the second stream within the tank 110 (or static mixer), is from about 20° C. to about 40° C. or from about 20° C. to about 30° C.

The cold process stream 104 may include a liquid emollient or solvent, which may be selected from the various liquid carriers described above. A few examples include mineral oil; PPG-14 butyl ether; isopropyl myristate; petrolatum; butyl stearate; cetyl octanoate; butyl myristate; myristyl myristate; C12-15 alkylbenzoate (e.g., Finsolv™); octyldodecanol; isostearyl isostearate; octododecyl benzoate; isostearyl lactate; isostearyl palmitate; isobutyl stearate; dimethicone, and any mixtures thereof.

The cold process stream 104 may also optionally comprise any heat sensitive component that could chemically degrade or deteriorate or react with components of the antiperspirant composition at elevated temperatures or corrode metal process equipment at elevated storage temperatures.

The first process stream 102 and the second process stream 104 are combined in, or just prior to entering, the mixing chamber 106. The mixing chamber 106 may comprise a pipe, or any other suitable arrangement capable of receiving both the first stream 102 and the second stream 104 therein so that the streams are combined therein with sufficient turbulence to cause thorough mixing and heat transfer. By controlling the ratio of the first process to the second process stream at the mixing chamber 104, it is possible to control the temperature $T_e$ of the mixture exiting the mixing chamber 106. The mixing chamber 106 may be a small void space containing static baffles 114 or other physical structure arranged to enable substantial and/or thorough mixing and heat transfer between the first and second streams 102, 104. The streams 102 and 104 may be introduced into the mixing chamber 106 in an opposed manner, one example of which is shown in FIG. 3, where the streams enter the mixing chamber at about 180° C. apart so that impaction of streams may significantly enhance their rapid mixing. While the streams 102 and 104 are shown entering the mixing chamber in an opposed manner, it will be appreciated that other arrangements may be utilized.

Upon exiting the mixing chamber 106, the mixture flows to an injector 120, which may take the form of piston pump, which pushes a volume of the hot mixture into a dispensing package. The injector 120 has a nozzle 122 having an exit opening through which the mixture is ejected or essentially poured or cast into the dispensing package at atmospheric pressure. Since the mixture upon exiting the nozzle 122 is still hot and has a look and consistency similar to milk, the pressure used to dispense the mixture from the nozzle can be very low (e.g. 10 psig, 5 psig, 4 psig or even 2 psig or less), although it is contemplated that other pressures within the injector 120 might be utilized if desired. In some instances, the mixture is able to self level within the dispensing package prior to solidifying. In some instances, only a single mixture or casting step is utilized to fill the dispensing package in order to form a single phase solid stick antiperspirant composition.

Dispensing packages 125 may be maneuvered into position for filling by any means known in the art, including conveyor 130. The dispensing packages 125 may be filled by top or bottom filling, as known in the art. A description of some examples of top and bottom filling processes is provided in commonly assigned USPN 2013/170886. The antiperspirant compositions cool within the dispensing package to ambient temperature to thereby form a solid stick antiperspirant composition.

The step of combining the at least one hot process stream and the at least one cold process stream together involves combining the streams in such a manner which may cause substantially complete mixing and heat transfer between the hot process stream and the cold process stream in a very short time period. The time period during which such mixing and heat transfer occur according to the present invention is less than 3 seconds, more specifically less than 1 second, although longer mix times may also be used. Further, it is believed that minimizing the amount of time from the moment that the antiperspirant active and the surfactant are mixed to the moment that the mixture exits the nozzles should be less than about 5, 4, 3, 2, or 1 minute in order to minimize the amount of time during which the antiperspirant active and surfactant interact prior to dispensing into the dispensing package. In some instances, the antiperspirant active and surfactant are in contact for about 1 minute or less while the structurant is above its crystallization onset temperature.

As discussed above, the temperature $T_e$ of the mixture exiting the mixing chamber 106 is preferably still hot. In some instances, the mixture exiting the mixing chamber may be from 10° C. to 15° C. or more above the onset of crystallization of the solid stick antiperspirant composition. In some instances, the mixture upon exiting the nozzle 122 may have an exit temperature from about 55° C. to about 60° C. or more. The mixture cools within the dispensing package, at which point one or more of the structurants may begin to crystallize. Preferably, complete mixing of the first process stream and the second process stream occurs within 3.5 inches, 2 inches or 1 inch of the where the first process stream and the second process stream enter the mixing chamber 106.

The temperature of the hot process stream, the cold process stream, and the resulting, combined, product stream can be measured by any method known in the art. The temperature of the hot process stream $T_h$ and the temperature of the cold process stream $T_c$ can be measured just before the two streams enter the mixing chamber 106 or otherwise combine; and the temperature $T_e$ of the mixture can be measured right after the hot and cold streams have been combined and exit the mixing chamber.

While the dual stream method is described herein with regard to two process streams, it will be appreciated that the process is not limited to mixing just two process streams; one skilled in the art will understand that each of the hot and cold process streams may comprise several hot or cold streams. Put another way, the present invention contemplates mixing multiple hot process streams and multiple cold process streams.

VI. Test Methods

Hygroscopicity

To determine hygroscopicity of an antiperspirant active, the following method may be used. Partially fill a glass desiccator (e.g., vwr catalog #25020-020) with a saturated solution of potassium chloride and seal appropriately. The desiccator is allowed to equilibrate for no less than 24 hours at 20° C. to create an 86% relative humidity environment. Next, weigh a metal weigh boat or pan and record the weight (Wt boat). Add approximately 2 grams of antiperspirant active to weigh boat and record the weight (Wt total). Place the weigh boat and antiperspirant active in the desiccator (above the saturated potassium solution) assuring the boat does not come in contact with the solution, and seal the desiccator appropriately. Allow the weigh boat and antiperspirant active to remain in the dessicator for 5 days at 20° C. Remove weigh boat and record weight (Wt total 5 days).

$$\text{Hygroscopicity} = \frac{(\text{Wt total 5 days} - \text{Wt boat}) - (\text{Wt total} - \text{Wt boat})}{\text{Wt total} - \text{Wt boat}}$$

Antiperspirant Composition Hardness

Antiperspirant solid stick compositions can be evaluated for hardness (gram-force) and defined in terms of penetration force values. "Penetration force value" as used herein can represent a force required to move a standard 45° angle penetration cone through the composition for a distance of 10 mm at a rate of 2 mm/second. Values can be measured at 27° C. and 15% relative humidity using a TA-XT2 Texture Analyzer, available from Texture Technology Corporation, Scarsdale, N.Y., U.S.A. Higher values represent a harder product and lower values represent a softer product. The cone is available from Texture Technology Corp., as part number TA-15, and can have a total cone length of about 24.7 mm, an angled cone length of about 18.3 mm, and a maximum diameter of an angled surface of the cone of about 15.5 mm. The cone can have a smooth, stainless steel construction and weigh about 17.8 grams.

To operate the TA-XT2 Texture Analyzer, the cone, or probe, can first be attached to a probe carrier arm and cleaned with a low-lint wipe. Subsequently, a top stop and a bottom stop can be checked to ensure each is in a desired position. Test samples will generally be the composition inside the consumer applicator. Once samples have been properly prepared by removing any top portion of the container so that the cone or probe has access to the composition in the package, a product sample can be placed on a test base. A template can be used to ensure the product sample is at a desired location on the test base such that the cone can be in a position to contact the product sample at a midpoint between a canister side and a canister screw.

After the cone can be adjusted to about 1 cm above the product sample, a "RUN" button on the Texture Analyzer can be pressed. A measurement can be taken by the Texture Analyzer while a canister containing the product sample is held. The cone can take a measurement and automatically disengage from the product sample. Two measurements can be taken for each canister.

Red Dot Method

A. Preparation of Starting Solutions:

A Phenol Red/Deionized Water solution (Deionized Water, 99.985% per weight; Phenol Red, 0.015% per weight) can be prepared as follows: Add Phenol Red powder to deionized water at room temperature based on the percentages noted. Stir for approximately 2 minutes at approximately 500 rpm, or until the powdered phenol red is completely dissolved into solution, using a magnetic stir bar and stir plate.

A Potassium Hydroxide/Deionized Water solution (Deionized Water, 95% per weight; Potassium Hydroxide (solid), 5% per weight) can be prepared as follows: Add Potassium Hydroxide pellets to deionized water at room temperature based on the noted percentages. Stir for approximately 1 minute at approximately 500 rpm, or until the potassium hydroxide is completely dissolved into solution, using a magnetic stir bar and stir plate.

B. Preparation of pH-Indicator Solution:

The pH-indicator solution can be prepared as follows: Weigh 200 grams of above Phenol Red/Deionized Water solution into a glass beaker. At ambient conditions, stir solution continuously at 100 rpm using a magnetic stir bar and stir plate. Insert calibrated pH probe, such as the Orion 8102BNV from Ross, into the solution. Measure the pH continuously. Adjust pH of Phenol Red/Deionized Water solution to 10.00+/−0.05 by adding 1 ml increments of Potassium Hydroxide/Deionized Water solution to the beaker containing the phenol red/deionized water solution while continually stirring.

C. Preparation of Antiperspirant Sample:

A film of the antiperspirant sample can be prepared using the following procedure. BYTAC TYPE VF-81 chemical resistant Norton FEP film is cut into 3×7 cm rectangles. A circle 2.2 cm in diameter is punched out. The protective back layer of the film is removed and the sticky side of the BYTAC film is adhered to a standard glass microscope slide. Care is taken such that the 2.2 cm circle cut out of the middle of the film is completely on the microscope slide. Antiperspirant is applied on the microscope slide in the center of the circle cut out of the BYTAC film. The antiperspirant sample is thoroughly spread throughout the circle by using a spatula or equivalent in a back and forth motion across the film surrounding the cut out circle. Spreading is continued until a smooth surface of antiperspirant product across the entire cut out circle is achieved. Carefully remove the BYTAC film from the microscope slide leaving behind the smooth, antiperspirant film. The antiperspirant film on the microscope slide is circular with a thickness equal to the thickness of the just removed BYTAC film (.about.0.1778 mm).

D. Application of pH Solution:

The antiperspirant film on the microscope slide is dried for 24 hours at ambient conditions (first drying period). After the first drying period, 20.0 microliters of the phenol red pH-indicator solution are applied to the center of the dried, antiperspirant sample using a standard micropipette such as the 5-50 microliter adjustable Finnpipette from Thermo Lab systems. The sample with the applied 20.0 microliters of phenol red ph indicator solution is left to dry for 24 hours at ambient conditions (second drying period).

E. Data Collection and Analysis:

During this second 24 hour drying period, the microscope slide with the dried antiperspirant film is placed face up on an approximate 15.24 cm×15.24 cm sample of black felt. A metal ring (1.8 cm diameter×2.5 cm height) is placed on the dried sample eliminating possible contamination of measurements by outside light sources. Care is taken to ensure the dried circle of phenol red ph solution is located in the center of the metal ring. A calibrated Minolta CR-300 series colorimeter, or equivalent, is placed on top of the metal ring. A standard spectral photometric measurement is taken and converted into standard L-a-b scale readings. At least four measurements are taken per sample. The average of the several (at least four) a-value readings is reported. Data can be collected at time points from 30 seconds after the phenol red indicator solution is added to up to 24 hours after the solution is added. This test is repeated three times per data time point and the results averaged.

Differential Scanning Calorimetry Method for Evaluating Complete Melt Point.

a. 10 mg of sample is weighed into a three-component volatile sample pan arrangement, comprising a bottom, a lid, and rubber seal. The assembled sealed pan resists loss of volatile components and is beneficial to accurately measure the melt points described herein.

b. The pan is then heated from 0° C. to 150° C. at a rate of 5° C./minute.

c. The complete melt point is determined as the temperature at the intersection of the baseline tangent to the trailing edge of the endothermic peak.

Figure 4:
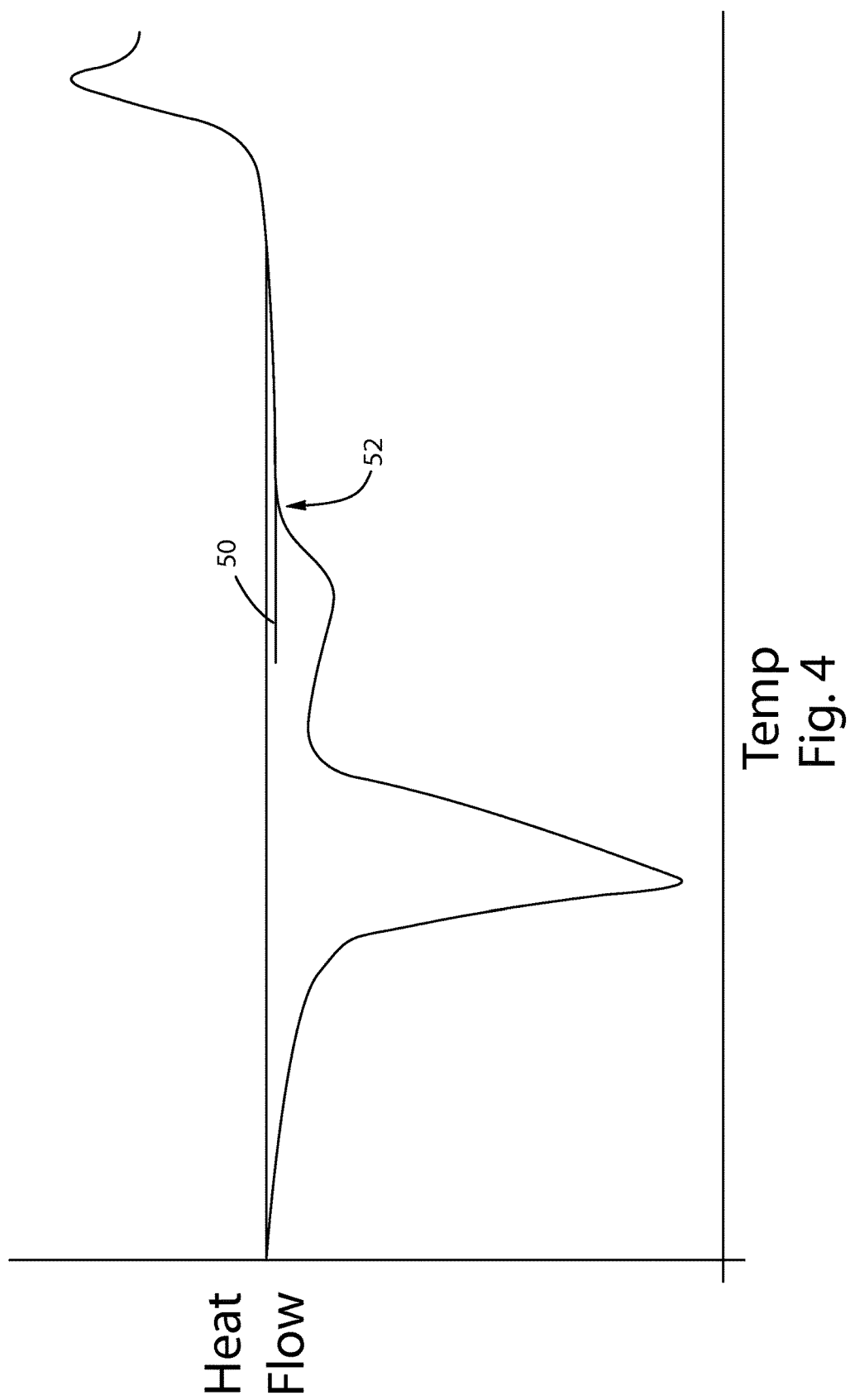
FIG. 4 is a non-limiting example of DSC cooling graph presented for purposes of illustration only, wherein a baseline tangent and a leading edge of a first, high temperature exothermic peak are shown.

Method for Determining Onset of Crystallization of a Solid Stick Antiperspirant Composition a. 10 mg of sample is weighed into a three-component volatile sample pan arrangement, comprising a bottom, a lid, and rubber seal. The assembled sealed pan resists loss of volatile components and is beneficial to accurately measure the melt points described herein.

b. The pan is then cooled from 100° C. to 0° C. at a rate of 5° C./minute.

c. The onset of crystallization is determined as the temperature at the intersection of the baseline tangent to the leading edge of the first, highest temperature exothermic peak. A non-limiting example of a cooling DSC curve is shown in FIG. 4, wherein the baseline tangent 50 and the leading edge of the first, high temperature exothermic peak 52 are shown for purposes of illustration only.

VII. Examples

The following examples are given solely for the purpose of illustration and are not to be construed as limitations of the invention as many variations thereof are possible without departing from the spirit and scope of the invention.

| Ingredients | Inventive Solid Stick Example #1 | Inventive Solid Stick Example #2 | Inventive Solid Stick Example #3 |
|---|---|---|---|
| SF1202 Silicone Fluid | 27.91 | 27.73 | 27.73 |
| Aluminum Zirconium Trichlorohydrex Gly | 26.49 | | |
| Aluminum Zirconium Tetrachlorohydrex Gly | | 26.67 | |
| Aluminum Zirconium Pentachlorohydrex Gly | | | 26.67 |
| Dow Corning 200 Fluid 10 Cst | | | |
| Tribehenin | | | |
| Synthetic Wax | | | |
| PPG-14 Butyl ether | 6.50 | 6.50 | 6.50 |
| C12-15 Alkyl Benzoate | 6.50 | 6.50 | 6.50 |
| 556 Cosmetic Fluid | 3.00 | 3.00 | 3.00 |
| Mineral Oil | 1.00 | 1.00 | 1.00 |
| Petrolatum | 3.00 | 3.00 | 3.00 |
| Stearyl Alcohol | 13.00 | 13.00 | 13.00 |
| Castor Wax MP-80 | 2.9 | 2.9 | 2.9 |
| Ozokerite | 1.00 | 1.00 | 1.00 |
| Behenyl Alcohol | 0.20 | 0.20 | 0.20 |
| C20-40 Pareth 10 ethoxylate | 2.00 | 2.00 | 2.00 |
| Talc | 2.50 | 2.50 | 2.50 |
| Cyclodextrin | 4.00 | 4.00 | 4.00 |
| | 100.00 | 100.00 | 100.00 |

Inventive Solid Stick Examples 1 and 2 were prepared by a dual stream process. In the hot stream tank, all of the waxes (stearyl alcohol, castor wax, ozokerite, behenyl alcohol), surfactant (C20-40 pareth 10 ethoxylate) and other emollients (C12-15 Alkyl benzoate, 556 Cosmetic fluid, petrolatum) and a lesser portion of the cyclopentasilaxane are adding into one tank mixed and heated to 88° C. to melt the waxes. In the cold stream tank, all of the powders (active, talc, cyclodextrin), perfumes, PPG-14 butyl ether, and a greater portion of the cyclopentasiloxane are added and mixed and maintained at ambient temperature less than 50° C. Once each of the hot and cold streams are adequately mixed so they are homogenous, each of the process streams are simultaneously fed into a static mixer where they combine for about 5 seconds or less, to ensure a homogenous product while minimizing the mix time. The mixture then exits the static mixing chamber into individual dispensing packages where it is allowed to cool to room temperature.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. In addition, U.S. Provisional Application Ser. No. 61/777,255 filed Mar. 12, 2013 is hereby incorporated by reference in its entirety. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A solid stick antiperspirant composition, comprising:
    an antiperspirant active comprising a zirconium salt, wherein the solid stick antiperspirant composition is substantially or completely free of aluminum zirconium tetrachlorohydrate glycine having a metal to chloride ratio from 1.2 to 1.3;
    a structurant comprising stearyl alcohol;
    a surfactant, wherein the surfactant has a melt temperature that is greater than the crystallization onset temperature of the solid stick antiperspirant composition;
    wherein the solid stick antiperspirant composition is a single phase; and
    wherein the contact time between the surfactant and active while mixed is less than 5 minutes.

2. A solid stick antiperspirant composition according to claim 1, wherein the antiperspirant active has a hygroscopicity greater than 30% at 86% relative humidity after 5 days and a metal to chloride ratio less than 1.5.

3. A solid stick antiperspirant composition according to claim 1, wherein the antiperspirant active has a hygroscopicity greater than 30% at 86% relative humidity after 5 days and a metal to chloride ratio greater than 1.3.

4. A solid stick antiperspirant composition according to claim 3, wherein the antiperspirant active is aluminum zirconium pentachlorohydrate glycine or aluminum zirconium pentachlorohydrex.

5. A solid stick antiperspirant composition according to claim 1, wherein the surfactant is a non-ionic ethoxylated linear alcohol having a carbon chain length from about 20 to about 40.

6. A solid stick antiperspirant composition according to claim 1, wherein the surfactant has an HLB value between about 6 and about 12.

7. A solid stick antiperspirant composition according to claim 1, wherein the surfactant has a melt temperature from 70° C. to 120° C.

8. A solid stick antiperspirant composition according to claim 1, wherein the surfactant has a concentration from about 1% to about 4% by weight of the solid stick antiperspirant composition.

9. A solid stick antiperspirant composition according to claim 1, wherein the structurant further comprises at least one material selected from the group consisting of hydrogenated castor wax, ozokerite, behenyl alcohol, polyethylene, polymethylene, and a triglyceride.

10. A solid stick antiperspirant composition according to claim 1, wherein the solid stick antiperspirant composition has a Red Dot Color Value of 0.5 or less at 4, 5, 10 and 15 minutes and a Red Dot Color Value greater than 1 at 30 seconds.

11. A solid stick antiperspirant composition according to claim 1, wherein the solid stick antiperspirant composition is anhydrous.

12. A solid stick antiperspirant composition according to claim 1, wherein the antiperspirant active has a concentration from 12% to 35% by weight of the solid stick antiperspirant composition.

13. A solid stick antiperspirant composition according to claim 1, wherein the solid stick antiperspirant composition has a hardness greater than 600 gram force.

14. A solid stick antiperspirant composition, comprising:
    aluminum zirconium pentachlorohydrate glycine or aluminum zirconium pentachlorohydrex;
    one or more structurants;
    a surfactant, wherein the surfactant has a melt temperature that is greater than the crystallization onset temperature of the solid stick antiperspirant composition;
    wherein the solid stick antiperspirant composition is a single phase; and
    wherein the contact time between the surfactant and active while mixed is less than 5 minutes.

15. A solid stick antiperspirant composition, comprising:
    an antiperspirant active comprising a zirconium salt, wherein the antiperspirant active has a metal to chloride ratio greater than 1.4;
    one or more structurants;
    a surfactant, wherein the surfactant has a melt temperature that is greater than the crystallization onset temperature of the solid stick antiperspirant composition;
    wherein the solid stick antiperspirant composition is a single phase; and
    wherein the contact time between the surfactant and active while mixed is less than 5 minutes.

* * * * *